US007491194B1

(12) United States Patent  
Oliwa

(10) Patent No.: US 7,491,194 B1
(45) Date of Patent: Feb. 17, 2009

(54) REMOTE CONTROL VALVE FOR URINE COLLECTION BAG

(76) Inventor: David Oliwa, 3400 Craig Dr. #1822, McKinney, TX (US) 75070

( * ) Notice: Subject to any disclaimer, the term of this patent is extended or adjusted under 35 U.S.C. 154(b) by 122 days.

(21) Appl. No.: 10/771,557

(22) Filed: Feb. 3, 2004

(51) Int. Cl.
*A61M 1/00* (2006.01)
*A61F 5/457* (2006.01)

(52) U.S. Cl. .................. 604/327; 604/353; 604/544
(58) Field of Classification Search ............ 604/327, 604/323, 915, 353, 508, 544; 4/480
See application file for complete search history.

(56) References Cited

U.S. PATENT DOCUMENTS

| 501,372 | A | * | 7/1893 | Sherman | 604/327 |
|---|---|---|---|---|---|
| 2,476,375 | A | * | 7/1949 | Kent | 604/353 |
| 3,357,430 | A | * | 12/1967 | Rosenberg | 604/353 |
| 3,931,650 | A | | 1/1976 | Miller | |
| D239,986 | S | * | 5/1976 | Artz | D3/226 |
| 4,065,199 | A | * | 12/1977 | Andre et al. | 439/498 |
| 4,300,129 | A | * | 11/1981 | Cataldo | 340/539.11 |
| 4,444,515 | A | * | 4/1984 | Clark | 368/279 |
| 4,449,971 | A | | 5/1984 | Cawood | |
| 4,631,061 | A | * | 12/1986 | Martin | 604/318 |
| 4,775,083 | A | * | 10/1988 | Burger et al. | 224/675 |
| 4,802,241 | A | * | 1/1989 | Vickers et al. | 455/344 |
| 4,951,817 | A | * | 8/1990 | Barletta et al. | 206/305 |
| 4,956,895 | A | * | 9/1990 | Hayasaka | 24/3.11 |
| 4,991,225 | A | * | 2/1991 | Holcomb et al. | 455/90.3 |
| 5,010,642 | A | * | 4/1991 | Takahashi et al. | 29/868 |
| 5,057,094 | A | * | 10/1991 | Abbey | 604/351 |
| 5,230,481 | A | * | 7/1993 | Wheeler et al. | 242/379 |
| 5,346,483 | A | * | 9/1994 | Thaxton, Sr. | 604/353 |
| 5,385,500 | A | * | 1/1995 | Schmidt | 446/73 |
| 5,397,315 | A | * | 3/1995 | Schmidt et al. | 604/323 |
| 5,439,456 | A | * | 8/1995 | Fabricant | 604/327 |
| 5,555,490 | A | * | 9/1996 | Carroll | 361/686 |
| 5,570,827 | A | * | 11/1996 | Wiesner | 224/587 |
| 5,643,236 | A | * | 7/1997 | Hadley | 604/353 |
| 5,673,819 | A | * | 10/1997 | Brunswig | 222/113 |
| 5,803,323 | A | * | 9/1998 | Hayashi et al. | 224/241 |
| 5,915,558 | A | * | 6/1999 | Girvetz | 206/534 |
| 6,012,181 | A | * | 1/2000 | Johnson et al. | 4/480 |

(Continued)

FOREIGN PATENT DOCUMENTS

EP   0 407 276 A2   1/1991

(Continued)

OTHER PUBLICATIONS

Leg Bag Valve by Lakeshore Assistive Technology, http://www.lakeshoretechonline.com, Oct. 23, 2003, p. 1.*

(Continued)

*Primary Examiner*—Tatyana Zalukaeva
*Assistant Examiner*—Paula L Craig
(74) *Attorney, Agent, or Firm*—Blakely Sokoloff Taylor & Zafman LLP

(57) ABSTRACT

A discreet apparatus for draining a urine collection bag worn by an incontinent person has an electrically operated drain valve coupled to a drain tube of the urine collection bag. A control device for remotely controlling the drain valve is adapted to be worn by the person. The control device is preferably disguised with an outward configuration resembling an article that is ordinarily carried or worn for other purposes.

4 Claims, 2 Drawing Sheets

U.S. PATENT DOCUMENTS

| | | | | |
|---|---|---|---|---|
| 6,066,164 | A | * | 5/2000 | Macher et al. ............... 607/96 |
| 6,090,087 | A | * | 7/2000 | Tsukada et al. ............. 604/327 |
| 6,132,408 | A | | 10/2000 | Lutz |
| 6,223,751 | B1 | * | 5/2001 | Park ........................... 128/885 |
| 6,459,371 | B1 | * | 10/2002 | Pike ........................ 340/539.1 |
| 6,471,680 | B1 | | 10/2002 | Cawood |
| 6,520,334 | B1 | * | 2/2003 | Hoover ....................... 206/534 |
| 6,526,603 | B1 | | 3/2003 | Murphy |
| 6,543,689 | B2 | * | 4/2003 | Sabella ....................... 235/449 |
| 6,945,965 | B2 | * | 9/2005 | Whiting ...................... 604/323 |
| 2002/0005340 | A1 | * | 1/2002 | Marmaropoulos et al. ............................................................ 200/61.58 R |
| 2002/0140849 | A1 | * | 10/2002 | Slatter et al. ............... 348/375 |
| 2002/0173758 | A1 | * | 11/2002 | Whiting ...................... 604/323 |
| 2004/0102723 | A1 | * | 5/2004 | Horst ............................. 601/5 |
| 2004/0143229 | A1 | * | 7/2004 | Easter ......................... 604/322 |

FOREIGN PATENT DOCUMENTS

| | | |
|---|---|---|
| EP | 0 506 292 A1 | 9/1992 |
| WO | WO 90/13951 * | 11/1990 |
| WO | WO 94/08552 A2 | 4/1994 |
| WO | WO 00/64519 A1 | 11/2000 |
| WO | WO 01/07107 | 2/2001 |

OTHER PUBLICATIONS

Bisgaard, H. et al., Fine particle mass from the Diskus inhaler and Turbuhaler Inhaler in children with asthma, European Respiratory Journal, 11: 1111-1115 (May 1998).

de Boer, A.H. et al., "Inhalation characteristics and their effects on In vitro drug delivery from dry powder inhalers, Part 1. Inhalation characteristics, work on breathing and volunteers' preference in dependence of the inhaler resistance," International Journal of Pharmaceutics 130: 231-244 (1996).

Dunbar, Craig A. et al., A Comparison of Dry Powder Inhaler Dose Delivery Characteristics Using a Power Criterion, PDA Journal of Pharmaceutical Science & Technology, 54(6): 4780484 (Nov./Dec. 2000).

Feddah, Majid R. et al., in-Vitro Characterisation of Metered Dose Inhalers Versus Dry Powder Inhaler Glucocorticoid Products: Influenece of Inspiratory Flow Rates, J. Pham. Pharmaceut. Sci. (www/ualberta.ca/-csps) 3(3): 317-324 (2000).

Koskela, T. et al., Efficacy of salbutamol via Easyhaler® unaffected by low inspiratory flow, Respiratory Medicine 94: 1229-1233 (Dec. 2000).

Nielsen, K.G. et al., Flow-dependent effect of formoterol dry-powder inhaled from the Aerolizer®, European Respiratory Journal, 10: 2105-2109 (Sep. 1997).

Richards, Robert and Saunders, Michael, Need for a comparative performance standard for dry powder inhalers, Thorax 48: 1186-1187 (Nov. 1993).

Ross, Danna L. and Schultz, Robert K., Effect of Inhalation Flow Rate on the Dosing Characteristics of Dry Powder Inhaler (DPI) and Metered Dose Inhaler (MDI) Products, Journal of Aerosol Medicine, 9: 215-226 (Nov. 2, 1996).

Smith, Karen J. et al., Influence of Flow Rate on Aerosole Particle Size Distributions from Pressurized and Breath-Actuated Inhalers, Journal of Aerosol Medicine, 11: 231-245 (Nov. 4, 1998).

* cited by examiner

REMOTE CONTROL VALVE FOR URINE COLLECTION BAG

BACKGROUND OF THE INVENTION

1. Field of the Invention

This invention relates generally to the collection of bodily waste. More particularly, the invention relates to urine collection bags worn by persons who are incontinent.

2. Background

Incontinence afflicts many persons, especially many who are confined to wheelchairs. Typically, such persons have a urine collection bag that is worn on the leg, commonly at or near the calf. Conventional collection bags have a drain tube to permit emptying of the contents. For many incontinent persons, particularly paraplegic and quadriplegic individuals, considerable effort is required to empty a collection bag. Often, the assistance of an attendant is required.

Because the difficulties associated with emptying conventional collection bags may reduce a person's independence and may also cause embarrassment, efforts have been made to provide incontinent persons, particularly those confined to wheelchairs, with a means for more conveniently draining a collection bag. For example, U.S. Pat. No. 3,931,650 discloses a disposal device for wheelchairs in which the collection bag drain tube is connected to a valve mounted on the wheelchair. The valve may be manually operated, as by a lever within reach of the wheelchair occupant, or may be electrically operated using a solenoid. The valve and control mechanism, being mounted to the wheelchair, is inherently conspicuous.

SUMMARY OF THE INVENTION

The present invention provides a discreet apparatus for draining a urine collection bag worn by an incontinent person, particularly such a person who is confined to a wheelchair. An electrically operated drain valve is coupled to a drain tube of the urine collection bag. A control device for remotely controlling the drain valve is adapted to be worn by the person. The control device is preferably disguised with an outward configuration resembling an article that is ordinarily carried or worn for other purposes, thereby concealing the true function of the device. Examples of such articles include a personal electronic device, such as a pager, cell phone or the like, a key fob, a belt buckle, a pen, a broach, a decorative pin, etc.

DETAILED DESCRIPTION OF THE INVENTION

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

Figure 1:
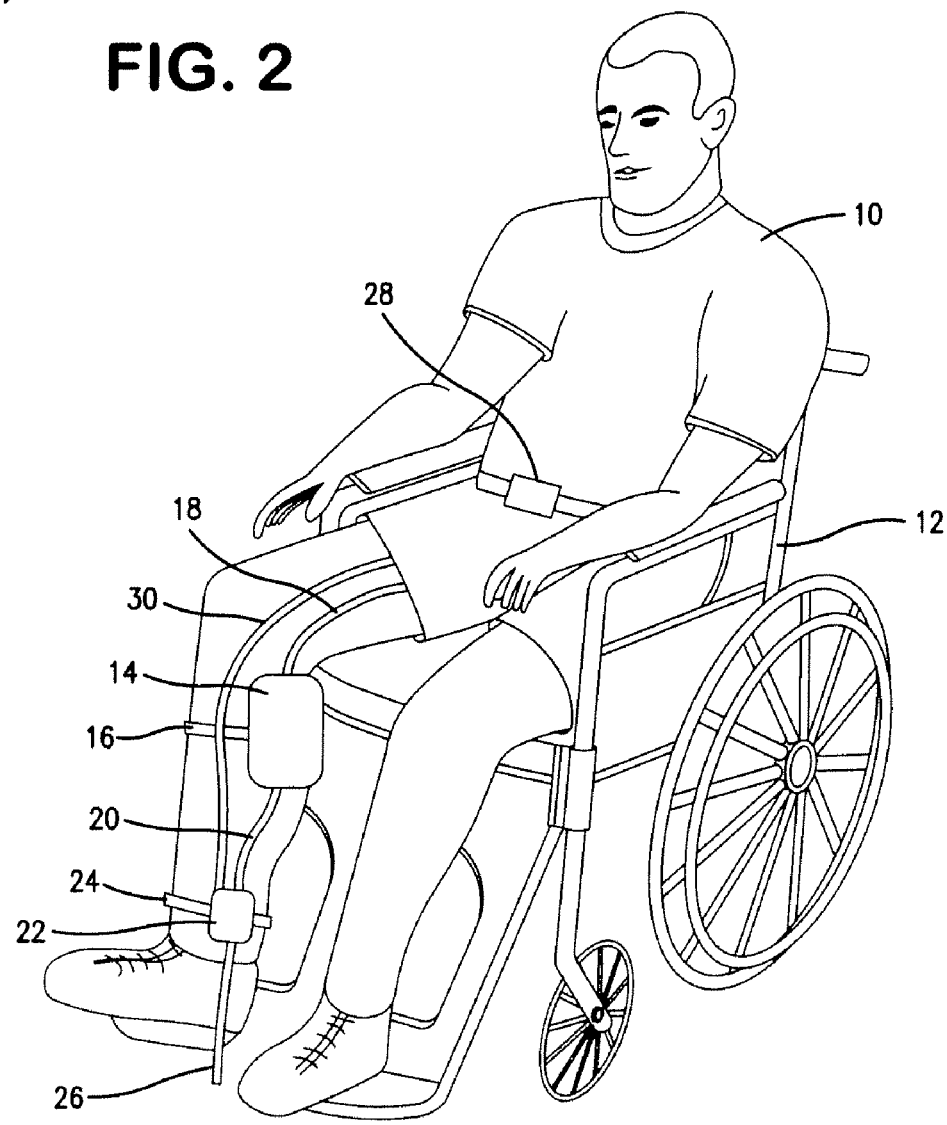
FIG. 1 illustrates the general configuration of a remote control valve in accordance with the present invention.
Figure 3A:
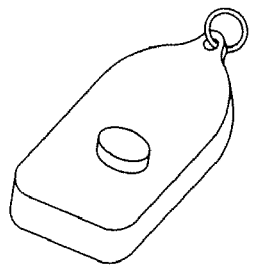
FIGS. 3A-3D illustrate alternative control device configurations.
Figure 3B:
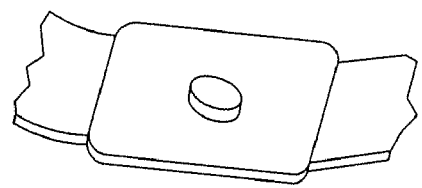
Figure 3C:
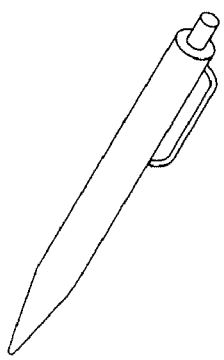
Figure 3D:
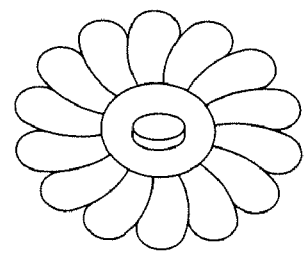

FIG. 1 generally illustrates the present invention as it may be employed by a person 10 confined to a wheelchair 12. A urine collection bag 14, commonly called a "legbag", is worn on the person's leg and is secured by strap 16. A catheter or other collection device drains into bag 14 through tube 18. Bag 14 drains through tube 20, which is connected to valve 22. A fine mesh filter may be incorporated within tube 20 or valve 22 to capture any stray materials.

Valve 22 is conveniently worn about the ankle and may be secured by an adjustable strap 24. Valve 22 is preferably enclosed within a soft padded case to prevent irritation of the person's skin. Strap 24 is also preferably made of a soft pliable material and may employ a hook and loop or other type of conventional closure device. An outlet tube 26 extends downwardly from valve 22 to a point just below the sole of the person's shoe.

Valve 22 is actuated by means of a low voltage solenoid. An electrical signal to operate the solenoid is sent from control device 28 through electrical cable 30. Cable 30 is preferably a flexible flat wire cable, which is able to withstand the daily abuse of being worn and protects the skin of the wearer by not leaving a "wire mark" on the skin, particularly near the waistband where cable 30 connects to control device 28. As will be explained more fully below, control device 28 may be disguised as a pager or similar personal electronic device that is commonly worn on a person's belt or waistband. Cable 30 preferably connects to device 28 at the rear thereof and is threaded over the belt or waistband to be routed through the pants leg to valve 22. It should be noted that the wheelchair-bound person would typically wear full-length pants, thereby concealing collection bag 14 and valve 22. Only outlet tube 26 would be visible below the pant cuff.

Valve 22 is preferably operated by a low voltage solenoid so that a suitable power source can be readily carried within control device 28 or within the enclosure for valve 22. The power source may comprise a disposable or rechargeable battery. For example, a 3.6 volt NiMH rechargeable battery may be used. Recharging may be accomplished with a conventional external charger or by means of a solar cell on device 28.

The fluid conducting portions of valve 22 are preferably constructed of materials that will not be corroded or otherwise degraded when conducting caustic fluids. Furthermore, the valve mechanism should be configured so that its sealing capability is not compromised by crystallization of the conducted fluid. The actuating solenoid should, of course, be compatible with the power source. The solenoid should also have a low holding current to maximize battery life. Assuming collection bag 14 has a capacity of 32 ounces and is elevated about one foot above valve 22, the valve is exposed to approximately 8.5 pounds of pressure. Thus, a relatively low force valve closure spring may be employed, thereby reducing the power required for actuation of the valve.

Figure 2:
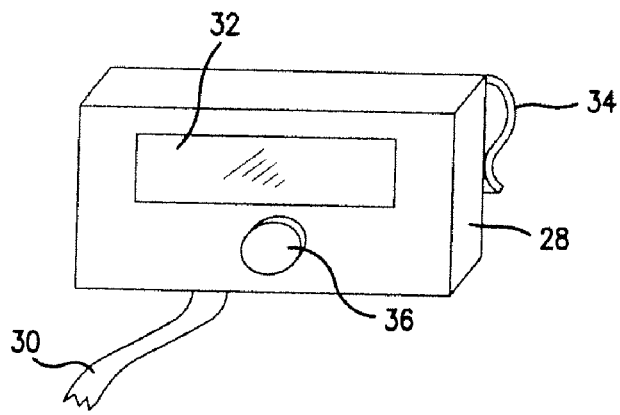
FIG. 2 is a detailed view of the control device in FIG. 1.

FIG. 2 is a detailed view of control device 28. As mentioned, the control device may be disguised as an article that a person might carry or wear for other purposes, such as a pager, cell phone or similar personal electronic device. Thus, the device may have a simulated display window 32. If a solar cell is used to maintain the charge of the power supply battery, the cell may be disposed within window 32. The device is secured to a belt or waistband with a clip 34 or other suitable means. Device 28, including clip 34, should be free of any sharp edges that might cause skin irritation or other discomfort.

Control device 28 includes a valve actuation control, such as a push button 36. A determined effort should be required to operate control 36 so that valve 22 is not inadvertently actuated, but the effort should not be so great as to be difficult for persons with limited manual strength or dexterity.

When it becomes necessary to empty to contents of collection bag 14, wheelchair 12 is maneuvered so that outlet tube 26 is positioned over a floor drain other suitable receptacle. Control 36 is then depressed to energize the solenoid for actuating valve 22. The dimensions of the fluid conducting path through valve 22 are preferably large enough to allow the contents of the collection bag, up to about 32 ounces, to completely drain within a reasonable period of time, such as 60 seconds or less.

In the foregoing description, control device 28 communicates with valve 22 via a wired connection 30. It will be appreciated that a wireless connection may also be employed using a radio frequency (RF) signal or other suitable means. In such case, control device 28 incorporates a small wireless transmitter and valve 22 incorporates a cooperating wireless receiver. Suitable transmitters and receivers for operating over short distances are well known. For example, a transmitter and receiver using the "Bluetooth" protocol may be employed. A wireless control device may be configured to resemble any of a variety of articles that are commonly carried or worn. For example, in addition to a personal electronic device as described above, the control device could be configured to resemble a key fob, belt buckle, pen, broach or decorative pin as shown in FIGS. 3A-3D, respectively.

It will be recognized that the above-described invention may be embodied in other specific forms without departing from the spirit or essential characteristics of the disclosure. Thus, it is understood that the invention is not to be limited by the foregoing illustrative details, but rather is to be defined by the appended claims.

What is claimed is:

1. An apparatus for draining a urine collection bag worn by a person comprising:
    an electrically operated drain valve coupled to a drain tube of the urine collection bag;
    a control device for remotely controlling the drain valve, the control device adapted to be worn by the person, the control device including a drain valve actuation control;
    a housing for the control device, the housing including a clip for securing the housing to a belt or waistband and further including a simulated display window such that the housing resembles a pager;
    a battery disposed within the housing for providing electrical power to operate the drain valve; and
    a strap having a hook and loop closure dimensioned and configured to secure the drain valve to the ankle of the person,
    wherein the control device is connected to the drain valve with a flexible flat wire cable.

2. The apparatus of claim 1 wherein the drain valve actuation control comprises a push-button switch.

3. An apparatus for draining a urine collection bag worn by a person comprising:
    an electrically operated drain valve coupled to a drain tube of the urine collection bag;
    a control device for remotely controlling the drain valve, the control device adapted to be worn by the person, the control device including a drain valve actuation control;
    a housing for the control device, the housing including a clip for securing the housing to a belt or waistband and further including a simulated display window such that the housing resembles a pager;
    a battery disposed within the housing for providing electrical power to operate the drain valve; and
    a strap having a hook and loop closure dimensioned and configured to secure the drain valve to the ankle of the person,
    wherein the control device is connected to the drain valve with a flexible wire cable.

4. The apparatus of claim 3 wherein the drain valve actuation control comprises a push-button switch.

* * * * *